US00PP07884P

United States Patent [19]

Zaiger et al.

[11] Patent Number: Plant 7,884

[45] Date of Patent: Jun. 16, 1992

[54] NECTARINE TREE "ARTIC GLO"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95351

[21] Appl. No.: 625,163

[22] Filed: Dec. 10, 1990

[51] Int. Cl.[5] ..... A01H 5/00

[52] U.S. Cl. ..... Plt./40

[58] Field of Search ..... Plt. 40, 41

*Primary Examiner*—James R. Feyrer

[57] ABSTRACT

A new and improved variety of nectarine tree which has the following unique combination of desirable features that are outstanding in a new variety.

1. Regular and productive bearer of white flesh clingstone fruit.
2. Fruit with excellent flavor and eating quality.
3. The fruit having firm white flesh with good handling and shipping quality.
4. Bearing fruit with an attractive red skin color.
5. Vigorous upright growth.

1 Drawing Sheet

ORIGIN OF THE VARIETY

The new and distinct variety of nectarine tree was originated by us in our experimental orchard located near Modesto, Calif., as a second generation seedling from a cross between two selected seedlings. The maternal parent originated from a seedling of an open pollinated Carnival Peach (U.S. Plant Pat. No. 2,144) crossed to a seedling originating from an open pollinated Fayette Peach (non-patented). The paternal parent was a white flesh nectarine seedling of unknown parentage. We grew and maintained a large number of second generation seedlings from this cross which gave a range of peaches and nectarines, both white and yellow flesh. The present variety exhibited the distinctive desirable fruit characteristics described above and was selected for asexual reproduction and commercialization.

ASEXUAL REPRODUCTION OF THE VARIETY

The present new nectarine variety was asexually propagated by us in our experimental orchard located near Modesto, Calif., by budding, and the asexually propagated trees shown that said characteristics of the tree and its fruit are established and transmitted through succeeding propagations.

SUMMARY OF THE VARIETY

The new and distinct variety of nectarine tree is of large size, vigorous, upright growth, and a regular and productive bearer of large size, firm, white flesh, clingstone fruit with excellent flavor and eating quality. In comparison to the white flesh nectarine Rose (U.S. Plant Pat. No. 1,421) with which it has certain characteristics in common, the new variety has a higher degree of attractive red skin color, has firmer flesh with greater handling and shipping quality.

BRIEF DESCRIPTION OF THE PHOTOGRAPHS

The accompanying color illustrations, by photographic reproduction, are of typical specimens of the foliage and fruit. The exterior and sectional view of the fruit are shown to expose flesh coloration with a stone remaining in place. The illustrations were taken shortly after being picked (firm ripe) and the colors are as nearly true as reasonably possible in a color representation of this type.

DESCRIPTION OF THE VARIETY

The following is a botanically detailed description of the new and distinct variety of nectarine tree based upon observations of the specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Density.*—Medium dense.
- *Form.*—Upright, usually pruned to vase shape.
- *Production.*—Productive.
- *Bearer.*—Regular.

Trunk:
- *Size.*—Medium to stocky.
- *Texture.*—Medium shaggy.
- *Color.*—Brown to dull brown.

Branches:
- *Size.*—Medium.
- *Surface.*—Smooth to medium rough.
- *Lenticels.*—Medium number. Medium size.
- *Color.*—Light brown.

Leaves:
- *Size.*—Medium to large. Average length—6". Average width—1½".
- *Texture.*—Smooth.
- *Margin.*—Crenate.
- *Form.*—Lanceolate. Pointed.
- *Thickness.*—Medium.
- *Glands.*—Globose. Average number 2— range 1 to 4. Located on upper portion of petiole and lower portion of leaf blade.
- *Petiole.*—Medium length. Medium thickness. Upper surface grooved.
- *Color.*—Upper surface— jade green to green (27-E-5) to (27-E-7). Lower surface—grayish green (28-E-6) to (28-E-7).

Flower Buds:
- *Size.*—Medium.
- *Length.*—Medium.
- *Shape.*—Plump.

Flowers:
- *Size.*—Large—showy.

*Blooming Period.*—Mar. 9, 1990 to Mar. 15, 1990. Varies slightly with climatic conditions.
*Pollen.*—Present.
*Color.*—Pink.

Fruit:
*Maturity when described.*—Firm ripe.
*Date of first picking.*—Jun. 9, 1990.
*Date of last picking.*—Jun. 16, 1990.
*Size.*—Large. Average diameter axially— 2¾". Average transversely in suture plane— 2¾".
*Form.*—Nearly globose. Only slightly elongated in suture plane.
*Suture.*—Shallow. Extends from stem to apex.
*Ventral surface.*—Slightly lipped.
*Base.*—Retuse.
*Cavity.*—Rounded. Average depth— ½". Average breadth— ⅝".
*Apex.*—Majority of fruit have slight point. Varies from round to slight point.

Skin:
*Thickness.*—Medium.
*Texture.*—Tough— tenacious to flesh.
*Tendency to crack.*—Very slight.
*Down.*—Wanting.
*Color.*—White to pale yellowish white ground color (2-A-1) to (2-A-2). Overspread with red (9-A-7) to (9-B-8).

Flesh:
*Ripens.*—Evenly.
*Texture.*—Firm, meaty.
*Fibers.*—Small, few, tender.
*Juice.*—Moderate.
*Flavor.*—Excellent. Sub-acid, mild.
*Eating quality.*—Excellent.
*Amygdalin.*—Undetected.
*Aroma.*—Moderate.

*Color.*—White (2-A-1). Slight pinkish white steaks near pit cavity (9-A-2) to (9-A-3).

Stone:
*Type.*—Clingstone.
*Size.*—Large. Average length— 1 5/16". Average width—1". Average thickness—¾".
*Form.*—Oval.
*Base.*—Straight.
*Apex.*—Pointed.
*Sides.*—Nearly equal.
*Surface.*—Irregulalry furrowed toward apex—usually pitted toward base.
*Tendency to split.*—Very slight.
*Color.*—Brown to reddish brown (9-E-6) to (9-E-8).

Use: Dessert.
*Market.*—Local and long distance.
Keeping quality: Good.
Shipping Quality: Good.

The tree, flowers and fruit may vary in slight detail due to variations in soil types, cultural practices and climatic conditions; the present botanical description is that of the variety grown under the ecological conditions prevailing near Modesto, Calif.

We claim:

1. A new and distinct variety of nectarine tree substantially as illustrated and described, characterized by its large size, upright growth and a regular and productive bearer of large size, firm, white flesh, clingstone fruit with excellent flavor and eating quality; the new variety is further characterized in comparison to the white flesh nectarine Rose (U.S. Plant Pat. No. 1,421) as having firmer flesh with greater handling and shipping quality and a higher degree of attractive red skin color.

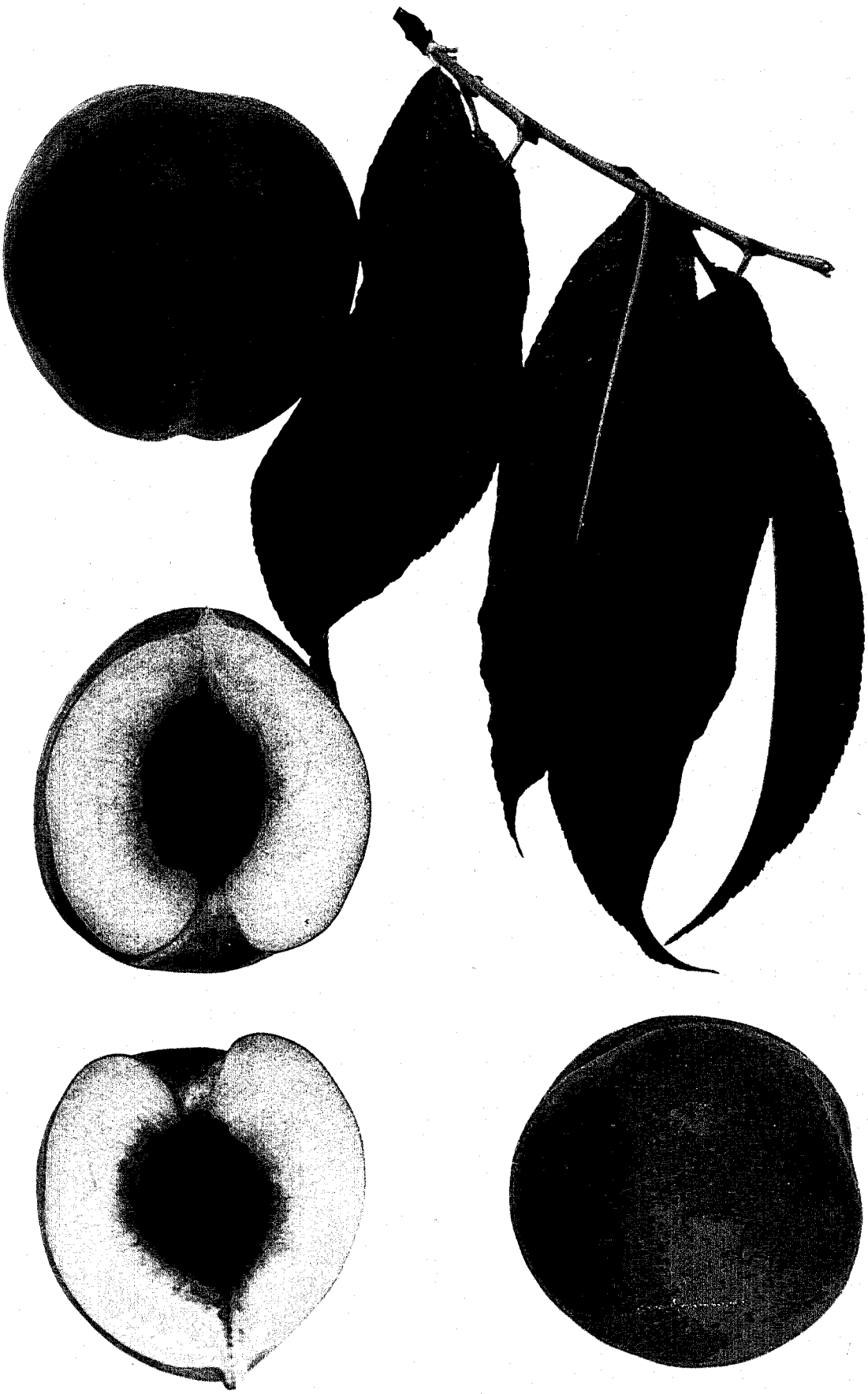

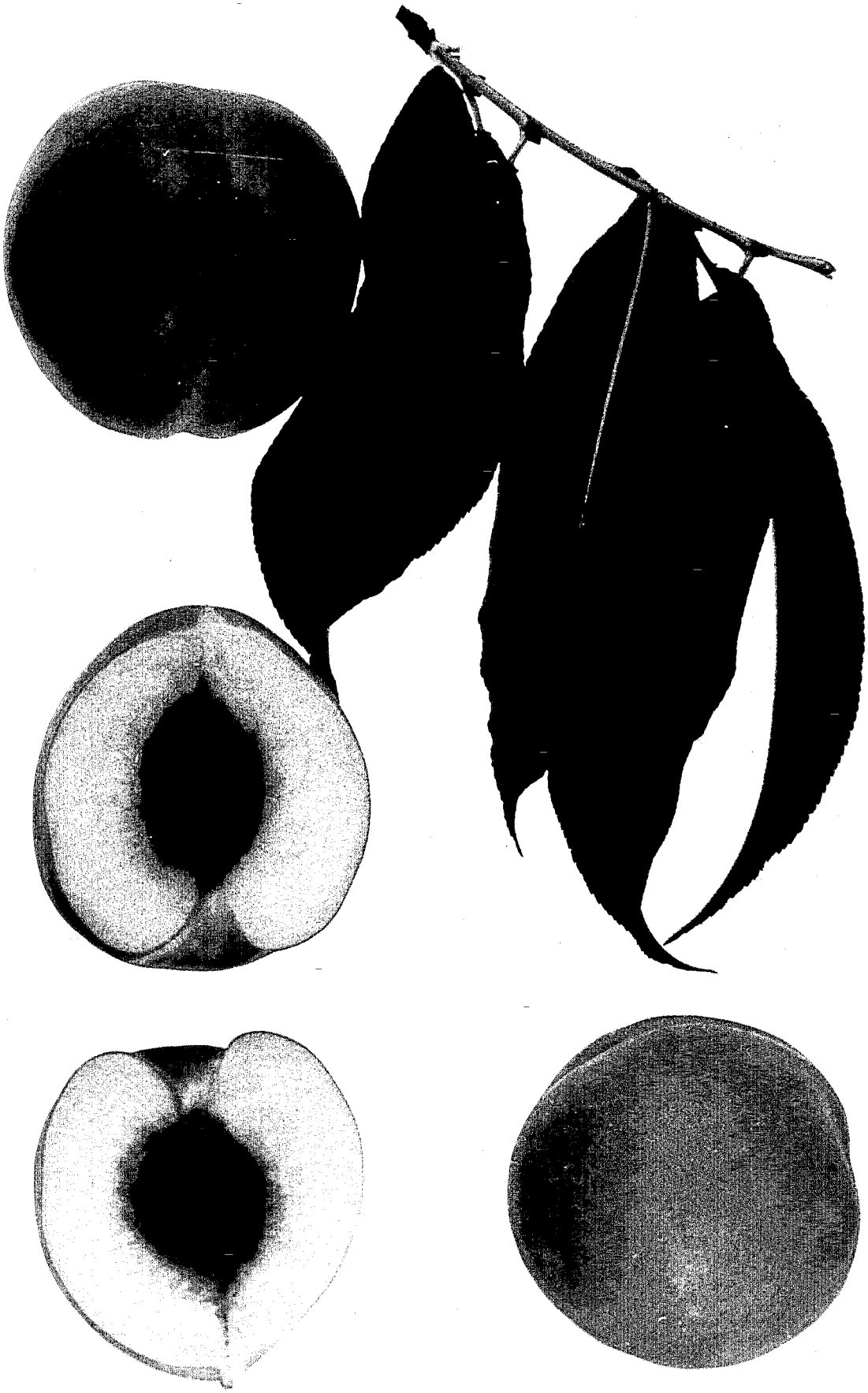

* * * * *